United States Patent
Borja et al.

(10) Patent No.: US 10,478,285 B2
(45) Date of Patent: Nov. 19, 2019

(54) DUAL OPTIC, CURVATURE CHANGING ACCOMMODATIVE IOL

(71) Applicant: NOVARTIS AG, Basel (CH)

(72) Inventors: David Borja, Fort Worth, TX (US);
Lauren Gerardi, Des Plaines, IL (US);
Shinwook Lee, Arlington, TX (US)

(73) Assignee: Novartis AG, Basel (CH)

( * ) Notice: Subject to any disclaimer, the term of this patent is extended or adjusted under 35 U.S.C. 154(b) by 44 days.

(21) Appl. No.: 14/920,663

(22) Filed: Oct. 22, 2015

(65) Prior Publication Data
US 2016/0256265 A1    Sep. 8, 2016

Related U.S. Application Data (60) Provisional application No. 62/127,338, filed on Mar. 3, 2015.

(51) Int. Cl.
*A61F 2/16*    (2006.01)

(52) U.S. Cl.
CPC .......... *A61F 2/1635* (2013.01); *A61F 2/1629* (2013.01); *A61F 2/1648* (2013.01); *A61F 2002/16901* (2015.04)

(58) Field of Classification Search
CPC ................. A61F 2/1629; A61F 2/1635; A61F 2002/16901
See application file for complete search history.

(56) References Cited

U.S. PATENT DOCUMENTS

| | | |
|---|---|---|
| 6,423,094 B1 | 7/2002 | Sarfarazi |
| 6,616,692 B1 | 9/2003 | Glick et al. |
| 7,122,053 B2 | 10/2006 | Esch |
| 7,217,288 B2 | 5/2007 | Esch et al. |

(Continued)

FOREIGN PATENT DOCUMENTS

JP    2007534364 A    11/2007

OTHER PUBLICATIONS

Dalton, M., "Whats ahead in 2010 New IOLs on the horizon", The Best of Ophthalmology . . . . Eye World News Magazine, Dec. 2009, 4 pages, Link: http://www.eyeworld.org/article-new-iols-on-the-horizon.

(Continued)

*Primary Examiner* — Leslie Lopez
(74) *Attorney, Agent, or Firm* — Baker Botts L.L.P.

(57) ABSTRACT

The present disclosure concerns a curvature-changing, accommodative intraocular lens (IOL) for implantation in the capsular bag of a patient's eye. The IOL includes a fluid optic body having a cavity for containing an optical fluid, the cavity at least partially defined by a sidewall extending around the cavity and defining a diameter of the cavity and a deformable optical membrane intersecting the sidewall around a circumference of the sidewall and spanning the diameter of the cavity. The IOL further includes a second optic body spaced a distance apart from the fluid optic body and a plurality of struts extending from the sidewall and coupling the fluid optic body to the second optic body. The struts are configured such that axial compression of the capsular bag causes the struts to deform the sidewall in a manner that increases the diameter of the cavity, modifying a curvature of the deformable optical membrane.

17 Claims, 7 Drawing Sheets

(56) References Cited

U.S. PATENT DOCUMENTS

| | | | |
|---|---|---|---|
| 7,261,737 B2 | 8/2007 | Esch et al. | |
| 7,485,144 B2 | 2/2009 | Esch | |
| 7,637,947 B2 | 12/2009 | Smith et al. | |
| 7,662,179 B2 | 2/2010 | Sarfarazi | |
| 8,048,155 B2 | 11/2011 | Shadduck | |
| 8,328,869 B2 | 12/2012 | Smiley et al. | |
| 8,361,145 B2 | 1/2013 | Scholl et al. | |
| 8,425,599 B2 | 4/2013 | Shadduck | |
| 8,454,688 B2 | 6/2013 | Esch et al. | |
| 2004/0082993 A1* | 4/2004 | Woods | A61F 2/1613 623/6.28 |
| 2005/0021139 A1 | 1/2005 | Shadduck | |
| 2005/0131535 A1* | 6/2005 | Woods | A61F 2/1613 623/6.37 |
| 2007/0260309 A1* | 11/2007 | Richardson | A61F 2/1613 623/6.34 |
| 2009/0005865 A1* | 1/2009 | Smiley | A61F 2/1613 623/6.13 |
| 2011/0282422 A1 | 11/2011 | Wulfman et al. | |
| 2011/0282443 A1 | 11/2011 | Smiley et al. | |
| 2011/0288638 A1 | 11/2011 | Smiley et al. | |
| 2012/0046744 A1 | 2/2012 | Woods et al. | |
| 2013/0103146 A1 | 4/2013 | Smiley et al. | |
| 2013/0268070 A1 | 10/2013 | Esch et al. | |
| 2013/0317607 A1 | 11/2013 | Deboer et al. | |
| 2014/0172092 A1 | 6/2014 | Carson et al. | |
| 2014/0180404 A1 | 6/2014 | Tran | |
| 2014/0249625 A1 | 9/2014 | Shadduck | |

OTHER PUBLICATIONS

Ben-Nun, J., et al, "The NuLens DYNACURVE IOL", Digital Supplement—Innovations in Ophthalmology 2011, 3 pages, Link: http://bmctoday.net/innovations2011/digital_supplement/article.asp?f=inno-2011-nulens.

O'heineachain, R., "Thermoplastic IOL fills capsule like natural lens", ESCRS, Dec. 2015, 3 pages, Link: https://www.escrs.org/Publications/eurotimes/04december/pdf/Thermoplastic.pdf.

Japan Patent Office, Japanese Office Action, Application No. 2017544603, dated Aug. 13, 2019, 8 pages.

* cited by examiner

FIG. 12

DUAL OPTIC, CURVATURE CHANGING ACCOMMODATIVE IOL

FIELD

This present disclosure relates generally to the field of intraocular lenses (IOLs) and, more particularly, to accommodative IOLs.

BACKGROUND OF THE DISCLOSURE

The human eye in its simplest terms functions to provide vision by receiving light through a clear outer portion called the cornea, and focusing the image by way of a crystalline lens onto a retina. The quality of the focused image depends on many factors including the size and shape of the eye, and the transparency and focal power of the cornea and the lens.

When age or disease causes the lens to become less transparent, vision deteriorates because of the diminished amount of light that is transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by zonules. Relaxation of the ciliary muscle applies an axial force that tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus on both near and far objects.

As the lens ages, it becomes harder and is less able to change shape in response to movements of the ciliary muscle. This makes it harder for the lens to focus on near objects, a medical condition known as presbyopia. Presbyopia affects nearly all adults by the age of 45 or 50.

When a cataract or other disease requires the removal of the natural lens and replacement with an artificial IOL, the IOL typically is a monofocal lens that provides a suitable focal power for distance vision but requires the use of a pair of spectacles or contact lenses for near vision. Multifocal IOLs, e.g., relying on diffractive patterns to general multiple foci, have been proposed but to date have not been widely accepted.

Therefore, a need exists for a safe and stable accommodative intraocular lens that provides accommodation over a broad and useful range.

SUMMARY OF THE DISCLOSURE

The present disclosure concerns curvature-changing, accommodative intraocular lenses (IOLs) that may be implanted in the capsular bag of a patient's eye and configured to harness the energy of the movement of the capsular bag upon contraction and relaxation of the ciliary muscles.

In certain embodiments, the IOLs described herein are designed such that axial compression of the capsular bag changes the shape of a fluid optic (e.g., a fluid-filled cavity defined in part by a deformable optical membrane), thereby altering the curvature of the membrane and the power of the optic. As just one example, the IOLs described herein may include a fluid optic body and a second optic body each disposed on the optical axis and configured to be in contact with a surface of the capsular bag, the fluid optic body and the second optic body being coupled via a plurality of struts.

Upon axial compression of the capsular bag, an axial compressive force on the struts (e.g., via the second optical membrane) may cause the struts to deform (e.g., to pivot or to bow out), resulting in an increase in the tension on the deformable optical membrane (i.e., the deformable optical membrane may stretch radially). As a result, the curvature of the deformable optical membrane may be reduced, as in a disaccommodated native lens.

Conversely, when axial compression is relaxed, the deformation of the struts may be relieved and the deformable optical membrane may become more rounded to provide for close vision, as in an accommodated native lens. For example, the plurality of struts can be biased to rotate in a direction opposed to the first direction upon relaxation of the axial compression. In accordance with various aspects of the present teachings, the IOLs described herein can be implanted into the native capsular bag to replace a cataractous or presbyopic natural crystalline lens removed therefrom.

In certain embodiments, an IOL includes a fluid optic body having a cavity for containing an optical fluid, the cavity at least partially defined by a sidewall extending around the cavity and defining a diameter of the cavity and a deformable optical membrane intersecting the sidewall around a circumference of the sidewall and spanning the diameter of the cavity. The IOL further includes a second optic body spaced a distance apart from the fluid optic body and a plurality of struts extending from the sidewall and coupling the fluid optic body to the second optic body. The struts are configured such that axial compression of the capsular bag causes the plurality of struts to deform the sidewall in a manner that increases the diameter of the cavity such that a curvature of the deformable optical membrane is modified.

Certain embodiments of the present disclosure may provide an IOL that has a relatively small size and/or occupies a limited volume of the capsular bag while still providing a substantial power change between its accommodated and disaccommodated state. Accordingly, the presently disclosed IOL may allow for smaller surgical incisions during implantation. Additionally, the shape and/or stiffness of certain embodiments of the presently disclosed IOL may allow for interaction of the IOL with the capsule in a manner that prevents posterior capsule opacification (PCO) and anterior capsule opacification (ACO) via square edge optics, open capsule, and mechanical procedure.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

Figure 1:
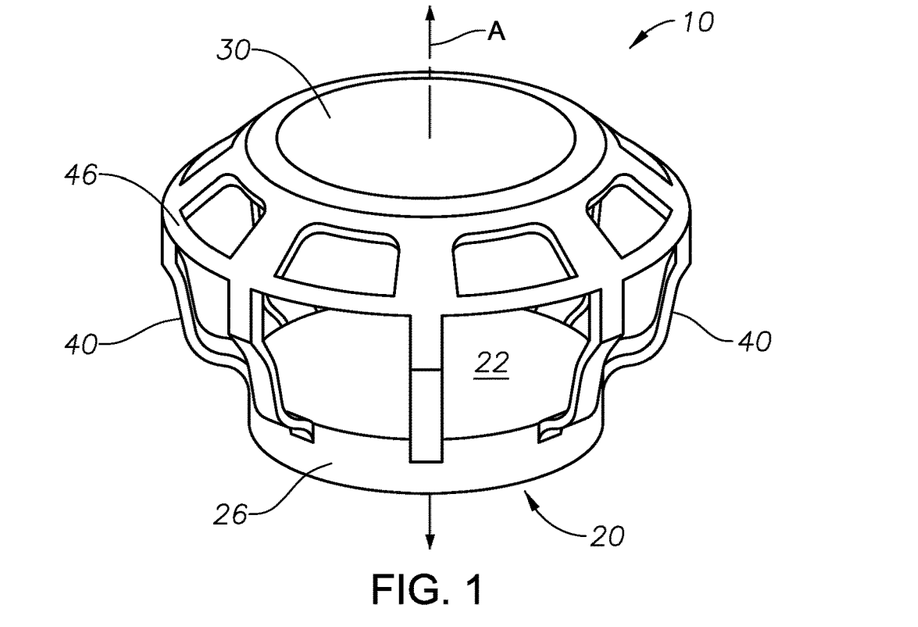
FIG. 1 is a perspective view of an exemplary curvature-changing, accommodative intraocular lens, according to certain embodiments of the present disclosure.
Figure 2:
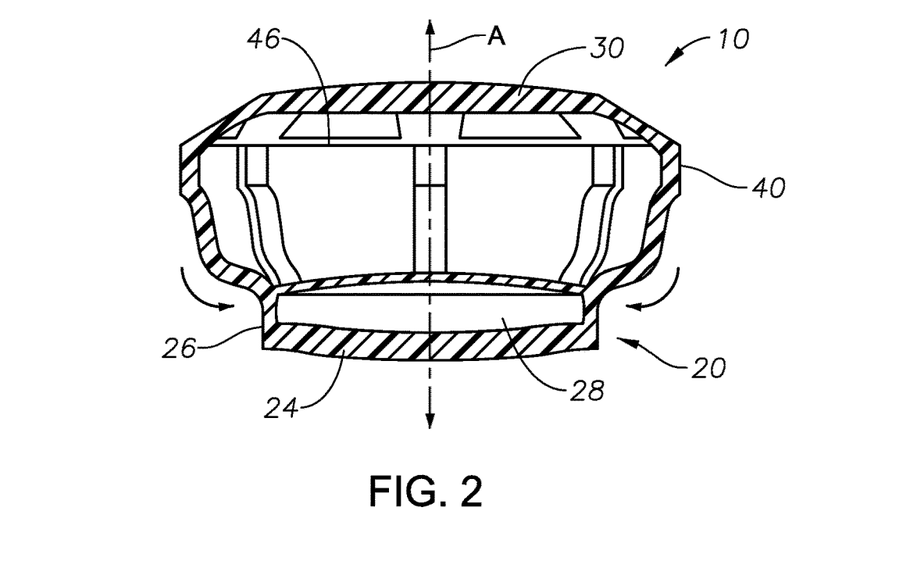
FIG. 2 is a cross-sectional view of the exemplary lens of FIG. 1.

The present disclosure generally relates to an intraocular lens (IOL) configured to be implanted in the capsular bag of a patient and that can utilize the movement of the capsular bag to change the power of the IOL. With reference to FIGS. 1 and 2, an exemplary IOL 10 is depicted, according to certain embodiments of the present disclosure. As shown in FIG. 1, the IOL 10 generally comprises a fluid optic body 20 and a second optic body 30 separated a distance apart. A plurality of struts 40 extend between the fluid optic body 20 and the second optic body 30 and couple the fluid optic body 20 to the second optic body 30, thereby defining a central space. In certain embodiments, another lens (e.g., as a solid lens) may be disposed in this central space, as discussed in detail below. When the IOL 10 is implanted within the capsular bag of a patient's eye such that the fluid optic body 20 and second optic body 30 are disposed on the optical axis (A) (allowing light traversing the IOL 10 to be refracted by fluid optic body 20 and/or second optic body 30), the compression of the capsular bag during disaccommodation can cause the plurality of struts 40 to deform (e.g., rotate, flex, bend, bow out) in manner that changes the shape of the fluid optic body 20, thereby altering the optical power of the IOL 10.

The fluid optic body 20 of IOL 10 can have a variety of configurations but generally comprises a sealed cavity for containing an optical fluid, the sealed cavity being at least partially defined by a deformable optical membrane. As best shown in FIG. 2, the fluid optic body 20 comprises a deformable optical membrane 22, a second optical membrane 24, and a circumferential sidewall 26 extending therebetween such that a sealed cavity 28 (which may contain an optical fluid) is formed within the fluid optic body 20. As discussed in detail below, the sidewall 26 can be coupled to the deformable optical membrane 22 such that rotation/flexion of at least a portion of the sidewall 26 (e.g., due to movement of the struts 40) increases tension on the deformable optical membrane 22. In certain embodiments, the second optical membrane 24 may be more rigid than the deformable optical membrane 22 so as to provide a relatively rigid surface upon which the axial force can be applied during compression of the capsular bag. For example, the second optical membrane 24 may be formed from a stiffer (e.g., less elastic) material than deformable optical membrane 22. Alternatively, the second optical membrane 24 may be formed of the same material deformable optical membrane 22 but may have an increased thickness relative to deformable optical membrane 22.

In certain embodiments, the junction of the second optical membrane 24 and the sidewall 26 can be a relatively-sharp edge (e.g., the surfaces may be substantially perpendicular to one another) so as to create a discontinuous capsular bend at this junction during compression of the capsular bag. Likewise, such a discontinuous bend can be generated at the anterior portion of the IOL 10, for example, via a circumferential lip about the anterior optic body 30.

Although the deformable optical membrane 22 is depicted and described herein as being located anterior to the second optical membrane 24 when disposed within the capsular bag 2 (such that the second optical membrane 24 contacts at least a portion of a posterior surface 6 of the capsular bag 2), the present disclosure contemplates that an IOL 10 may alternatively be configured such that, when implanted within the capsular bag 2, the deformable membrane 22 may be located posterior to the deformable membrane 22 (such that the second optical membrane 24 contacts at least a portion of an anterior surface 4 of the capsular bag 2).

The second optic body 30 of IOL 10 may include any suitable optic body facilitating the functionality described herein. For example, as depicted in FIGS. 1-2, second optic body 30 may comprise a solid (i.e., second optic body 30 may lack a cavity). As a result, second optic body 20 may provide a relatively rigid surface upon which the axial force during compression of the capsular bag may be applied. As another example, second optic body 30 may comprise a fluid optic similar to fluid optic body 20. In other words, IOL 10 may comprise both an anterior fluid optic (e.g., second optic body 30) and a posterior fluid optic (e.g., fluid optic body 20) each of which comprises a deformable optical membrane that changes shape upon axial compression of the capsular bag.

The fluid optic body 20 and the second optic body 30 of IOL 10 may each comprise a variety of materials that include, for example, fluid impermeable and biocompatible materials. In particular, the deformable optical membrane 24 and the second optical membrane 24 may each be constructed of materials that are optically transparent and smooth (e.g., an optical-quality surface). Exemplary materials include, hydrogels, silicones, acrylic materials, and other elastomeric polymers and soft plastics. For example, the silicone materials can be unsaturated terminated siloxanes, such as vinyl terminated siloxanes or multi-vinyl terminated siloxanes. Non-limiting examples include vinyl terminated diphenylsiloxane-dimethylsiloxane copolymers, vinyl terminated polyphenylmethylsiloxanes, vinyl terminated phenylmethylsiloxane-diphenyidimethylsiloxane copolymers, vinyl terminated polydimethylsiloxanes and methacrylate, and acrylate functional siloxanes. In other embodiments the lens-forming materials can be a hydrogel or a hydrophobic acrylic, such as the AcrySof® acrylic. Use of elastic/flexible materials can also enable the IOL 10 or optic body 20 to be folded upon itself during implantation, thereby decreasing the size of the incision required to insert the IOL 10 into the capsular bag 2. The present disclosure contemplates that fluid optic body 20 and the second optic body 30 may be constructed of the same or different materials.

In certain embodiments, fluid optic body 20, second optic body 30, and struts 40 can comprise a unitary body formed of the same material throughout, though these portions may vary in thickness in order to provide for desired movement of the IOL 10, as otherwise discussed herein. For example, second optic body 30 may be thicker than struts 40 and sidewall 26 such that the second optic body 30 provides structural support to the IOL 10 during axial compression of the capsular bag and efficiently transfers the axial force to the struts 40, the sidewall 26, and ultimately to the deformable optical membrane 22. Likewise, the second optical membrane 24 may be thicker relative to the sidewall 26 and deformable optical membrane 22 such that the second optical membrane 24 may also provide structural support for the IOL 10 upon axial compression of the capsular bag. Additionally, this configuration may allow the sidewall 26 to flex or rotate in response to the deformation of struts 40, thereby tensioning/stretching the deformable optical membrane 22.

In certain embodiments, various portions of the IOL 10 may be made of materials of different stiffness to provide for desired movement of the IOL 10, as otherwise discussed herein. For example, the deformable optical membrane 22 may be made of an elastomeric material having a low modulus, while the second optical body 30 and second optical membrane 24 may be of a more rigid material.

The various components of IOL 10 may each have any suitable configuration facilitating accommodation as described herein. For example, fluid optic body 20 and second optic body 30 may each have substantially circular cross sections. Alternatively, fluid optic body 20 and second optic body 30 may each have non-circular cross sections (e.g., oval or elliptical cross-section). Additionally, the sidewall 26 of fluid optic body 20 may have any suitable configuration that facilitates rotation/flexion in response to deformation of the attached struts 40. For example, the sidewall 26 may define a diameter 27 of the fluid optic body 20, and the deformable optical membrane 22 may span that diameter. Upon axial compression of the capsular bag (in the direction indicated by the arrows in FIG. 2), struts 40 may impart a force on the sidewall 26, thereby causing deformation of the sidewall 26 in a manner that cause the diameter 27 defined by the sidewall to increase. In particular, the sidewall 26 may deform such that at least a portion of the sidewall 26 rotates about a pivot. This increase in diameter 27 of sidewall 26 may cause a change in the radius of curvature of the deformable optical membrane 22 (e.g., by radially stretching the deformable optical membrane 22).

The present disclosure contemplates that the term "diameter" may encompass multiple diameters in the case of a fluid optic body 20 having a non-circular cross section (e.g., an elliptical cross section having a transverse and conjugate diameter). Moreover, when the term "diameter" encompasses multiple diameters, deformation of the sidewall in a manner that increases the diameter defined by the sidewall to increase may encompass an increase in one or more of those diameters.

The optical fluid contained within the cavity 28 of IOL 10 may be any suitable fluid and may include, for example, an incompressible or substantially incompressible fluid exhibiting an index of refraction different that the fluid surrounding the IOL 10. As a result, light passing through the IOL 10 may undergo refraction at both the deformable optical membrane 22 and the second optical membrane 24, the level of refraction being dependent upon the shape of the boundary between the optical fluid and the external fluid (i.e., the shape of the deformable optical membrane 22 and the second optical membrane 24 relative to the optical axis(A)). Exemplary suitable fluids for use in the cavity 28 include fluids with an index of refraction higher than water, for example, an index of refraction greater than 1.3. In certain embodiments, the fluid may exhibit an index of refraction greater than 1.36 or greater than 1.38. In other embodiments, the index of refraction may be in the range of about 1.3 to about 1.8, in the range of about 1.36 to about 1.70, or in the range of about 1.38 to about 1.60. Suitable fluids may include saline, hydrocarbon oils, silicone oils, and silicone gels.

The optical fluid may be disposed within the cavity 28 during fabrication of the IOL 10, after fabrication but before implantation of the IOL 10, or after implantation of the IOL 10. For example, the optic body 20 may include a fill port that can be sealed or plugged after filling the cavity 28. Additionally or alternatively, the optical fluid may be injected through the optic body 20 and the optic body 20 may be self-sealing.

The plurality of struts 40 may have any suitable configuration facilitating accommodation of the IOL 10 as described herein. For example, each of the plurality of struts 40 may generally extend between the fluid optic body 20 and the second optic body 30 (thereby coupling the fluid optic body 20 to the second optic body 30) and may be configured to move or deform in response to axial compression of the capsular bag (as described in detail below). In particular, as shown in FIG. 1, each of the plurality of struts 40 may extend in a direction substantially parallel to the optical axis (A) and couple a point or region on the circumference of the fluid optic body 20 to a point or region on the circumference of the second optic body 30. Although a particular number of struts 40 are depicted, the present disclosure contemplates any suitable number of struts 40 facilitating to translation of axial compression of the capsular bag into modification of the curvature of at least the deformable optical membrane 22.

In certain embodiments, each of the struts 40 may be curved. As a result, the axial force imparted by the capsular bag may tend to increase radial bowing of the struts 40. As a result, the maximum diameter of the IOL 10 in the disaccommodated state may be increased.

In certain embodiments, struts 40 may have cross-sectional areas that varies with length so as to provide additional support and/or to provide for the movement of the struts 40 as discussed herein. For example, portions of a struts 40 that are closer to the fluid optic body 20 (e.g., the posterior end of the strut 40) may be thinner relative to the portions of the strut 40 closer to the second optic body 30 (e.g., the anterior end of the strut). As a result, the posterior end of the strut 40 may move in response to axial compression so as to increase the deformation of the deformable optical membrane 22.

In certain embodiments, adjacent struts 40 may be coupled to one another via a ring-like structure 46 disposed around the circumference of the IOL 10. Ring 46 may increase stability of the IOL 10 within the capsular bag and/or improve the uniformity of the force exerted on the struts 40 and deformable membrane 22 as the IOL 10 is axially compressed. Additionally, the axial force exerted on the second optic body 30 may be more evenly distributed between the struts 40 due to their coupling with the ring 46, and the ring 46 may provide additional support to the struts 40 at a location between the fluid optic body 20 and the second optic body 30 in which stress on the struts 40 during axial compression is concentrated.

In certain embodiments, the fluid optic body 20, the second optic body 30, and the struts 40 may each be dimensioned such that, in its resting state (as shown in FIG. 2), the IOL 10 may have a length along the optical axis (A) that is slightly larger than the anterior-to-posterior depth of the capsular bag. As a result, tension exerted by the capsular bag on the IOL 10 upon implantation may substantially maintain the IOL 10 in a desired position. Additionally, the fluid optic body 20, the second optic body 30, and the struts 40 may each be dimensioned such that the surface area that engages the anterior and posterior surfaces of the capsular bag is maximized while minimizing the overall volume of the IOL 10. For example, the radial dimensions of the IOL 10 may be slightly smaller than diameter of the capsular bag to help maximize the transfer of energy to the IOL 10 by minimizing loss of energy due to lateral stretching of the IOL 10.

Figure 3A:
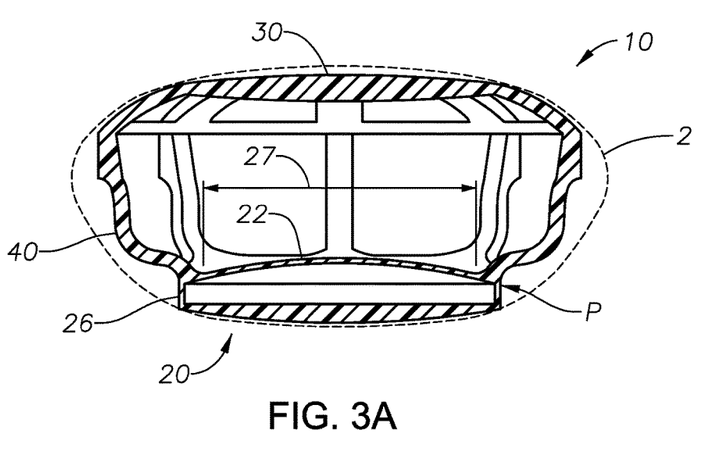
FIG. 3A is a cross-sectional view of the exemplary lens of FIG. 1, depicting the lens in its accommodated (close vision) state within the capsular bag.
Figure 3B:
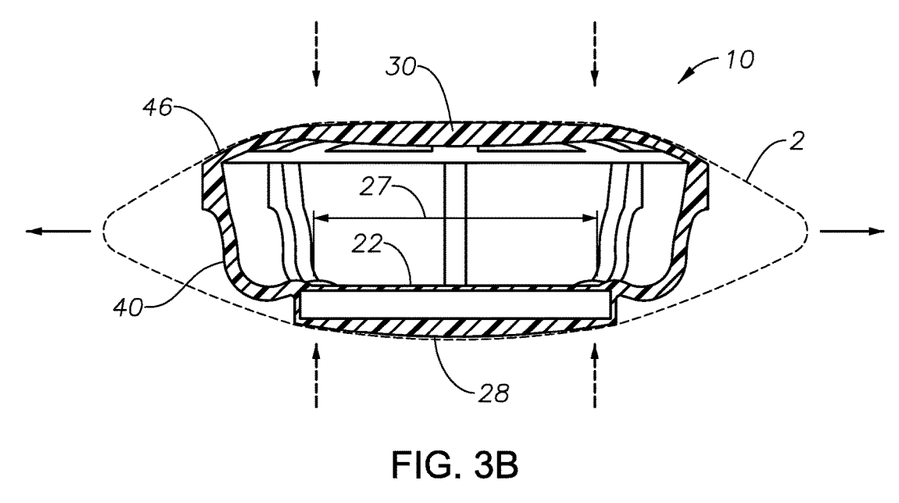
FIG. 3B is a cross-sectional view of the exemplary lens of FIG. 1, depicting the lens in its disaccommodated (near vision) state within the capsular bag.

Movement of the exemplary IOL 10 will now be described as the capsular bag 2 goes from an accommodated state, as shown in FIG. 3A, to a disaccommodated state, as shown in FIG. 3B. With reference first to FIG. 3A, the IOL 10 and capsular bag 2 are depicted in their accommodated state during which the ciliary muscles are contracted such that zonules extending between the ciliary muscles and the capsular bag 2 are slack. As a result, there exists little radial tension on the capsular bag 2. As discussed above, IOL 10 may be sized such that, in this state, the fluid optic body 20 and the second optic body 30 may each be in contact with the capsular bag 2, but the capsular bag 2 may exert a minimum amount of axial force on the IOL 10. This minimum amount of axial force may help maintain the IOL 10 in a desired position within the capsular bag 2.

Upon relaxation of the ciliary muscles, the zonules will exert radial tension on the capsular bag 2 (as indicated by the solid arrows in FIG. 3B), which causes axial compression of the capsular bag 2 (as indicated by the broken arrows). As a result, the capsular bag 2 may exert a force on the IOL 10 (specifically fluid optic body 20 and second optic body 30), and this force may cause a decrease in the separation distance between fluid optic body 20 and second optic body 30. This decrease in the separation distance between fluid optic body 20 and second optic body 30 may contribute to the optical power change of the IOL 10. However, the primary factor affecting the optical power change of the IOL 10 may be the curvature change of the deformable optic membrane 22 resulting from deformation of struts 40, as discussed further below.

As is illustrated by comparing FIGS. 3A and 3B, the maximum diameter of IOL 10 (e.g., the diameter measured at the ring 46) may increase due deformation of struts 40 resulting from axial compression of the capsular bag 2. In particular, the posterior-curved portions of the struts 40 located adjacent to fluid optic body 20 may move radially and/or posteriorly (e.g., through rotation about the fluid optic body 20). Because the posterior-most ends of struts 40 are coupled to the sidewall 26, such deformation of the struts 40 may impart a force upon the sidewall 26 and cause deformation of the sidewall 26. For example, at least a portion of the sidewall 26 may rotate outward about a pivot such that the diameter 27 defined by the sidewall 26 increases. In certain embodiments, the portion of sidewall 26 defining diameter 27 (i.e., the point at which sidewall 26 and deformable optical membrane 22 intersect) may anteriorly raise the periphery of the deformable optic membrane 22. Deformation of sidewall 26 in a manner that increases diameter 27 may increase tension and radial stretching of the deformable membrane 22. As a result, the deformable optical membrane 22 may exhibit a flatter profile (e.g., a larger radius of curvature). Additionally, the distance between the deformable optical membrane 22 and the second optical membrane 24 (along the optical axis (A)) may be decreased. As the radial force on the capsular bag 2 is relaxed, the capsular bag 2 and IOL 10 may return to their biased configuration shown in FIG. 2.

Figure 4A:
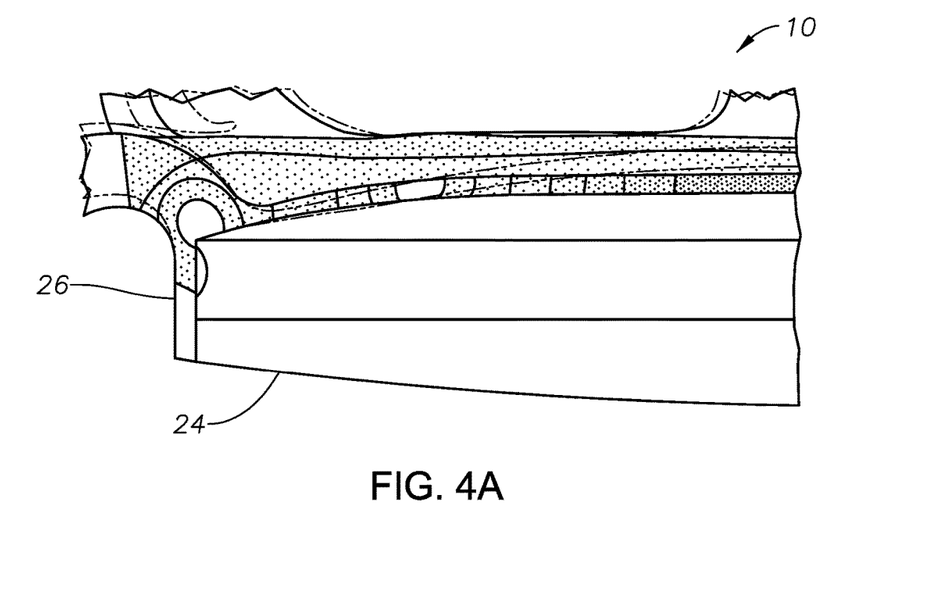
FIG. 4A is a simulation of the pivoting of the struts and the curvature change of the deformable optical membrane of the exemplary lens of FIG. 1 as it moves from an accommodated state to a disaccommodated state.
Figure 4B:
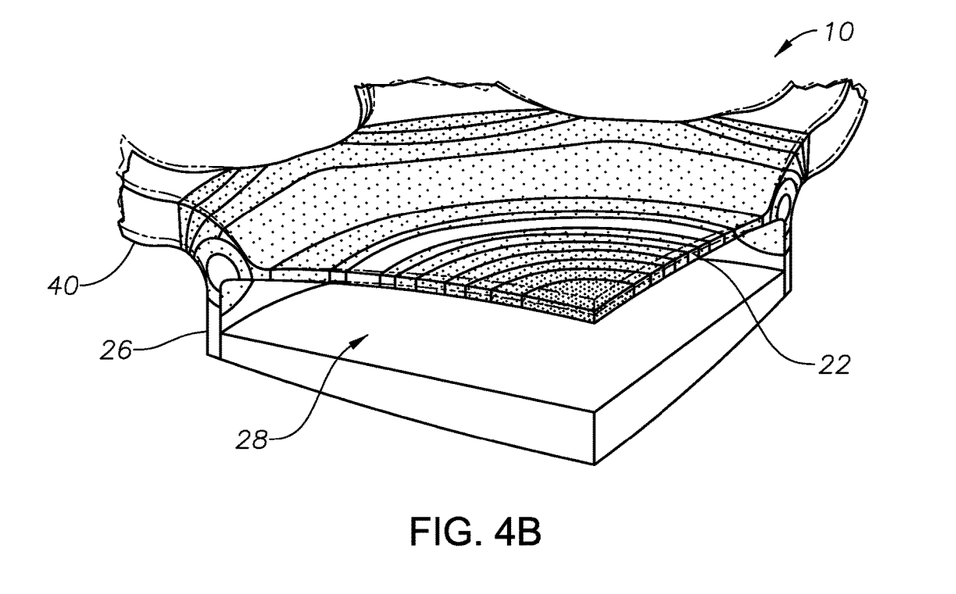
FIG. 4B is another view of the simulation of the pivoting of the struts and the curvature change of the deformable optical membrane of the exemplary lens of FIG. 1 as it moves from an accommodated state to a disaccommodated state.

With reference now to FIGS. 4A and 4B, finite element analysis of exemplary simulated movement of the IOL 10 is depicted as the IOL 10 moves from its resting or accommodated state (as shown in phantom outline) to its disaccommodated state (as shown in solid color). Upon axial compression of the capsular bag, the axial compressive force on the IOL 10 increases, initiating movement of the struts 40 and deformation of the sidewall 26. This movement of struts 40 transfers at least a portion of the force exerted on IOL 10 to the sidewall 26, which in turn transfers at least a portion of that force to deformable optical membrane 22. The resulting stress on deformable optical membrane 22 is at a maximum along the optical axis as the deformable optical membrane 22 is pulled from all sides. As compression continues, the struts 40 rotate further and the cavity 28 containing the optical fluid changes shape as the deformable optical membrane 22 becomes flatter.

As the thickness of the sidewall 26 increases and/or its height decreases, the overall power change of the IOL 10 during compression may decrease or a greater axial compressive force to achieve the same deformation may be required. In order to achieve maximum power change, the thickness of the sidewall 26 (i.e., in a radial direction) may be significantly less than its height (i.e., along the optical axis (A)). Additionally, increased thickness of the junction of the deformable optical membrane 22 and the sidewall 26 may help in distributing the deformation from the struts 40 more uniformly on the optic membrane 22, which may reduce the number of struts 40 needed without inducing optical aberrations in the deformable optical membrane 22.

The present disclosure contemplates that the thickness of the deformable optical membrane 22 may be manipulated (e.g., increased, decreased, and/or varied about its area) so as to maintain good visual acuity and high power change throughout accommodation. For example, a convex deformable optical membrane 22 (i.e., a membrane in which the central portion is thicker than the periphery) with a low power may reduce aberrations during accommodation. Alternatively, if the deformable optical membrane 22 is flat (i.e., the membrane exhibits a substantially constant thickness), it will deform more easily in the central part than the periphery. Additionally, the present disclosure contemplates that each surface of the IOL 10 within the optical aperture lens can be spherical or aspheric so as to alter the optical properties of light traversing therethrough. For example, the various surfaces of the second optic body 30 provide various locations to include complex optical designs, in accordance with that process as known in the art and modified in accordance with the present teachings.

The above-described IOL 10 may be fabricated using any suitable techniques known in the art and modified in light of the present teachings. For example, IOL 10 may be injection molded such that the struts 40 and deformable optical membrane 22 can be biased to the position shown in FIG. 2. That is, in the absence of substantial external forces (e.g., in its free form outside the eye), the IOL 10 can be configured to maintain a radius of curvature approximate its shape in an accommodated state. Accordingly, the struts 40 would tend to return to this biased position upon removal of or relaxation of the axial compressive force (e.g., as the capsular bag goes from its disaccommodated configuration to its accommodated configuration). This biased configuration may especially aid those patients in which the ciliary bodies have lost some of their contractility or the capsular bag 2 has lost some of its elasticity, for example, due to age.

Figure 5:
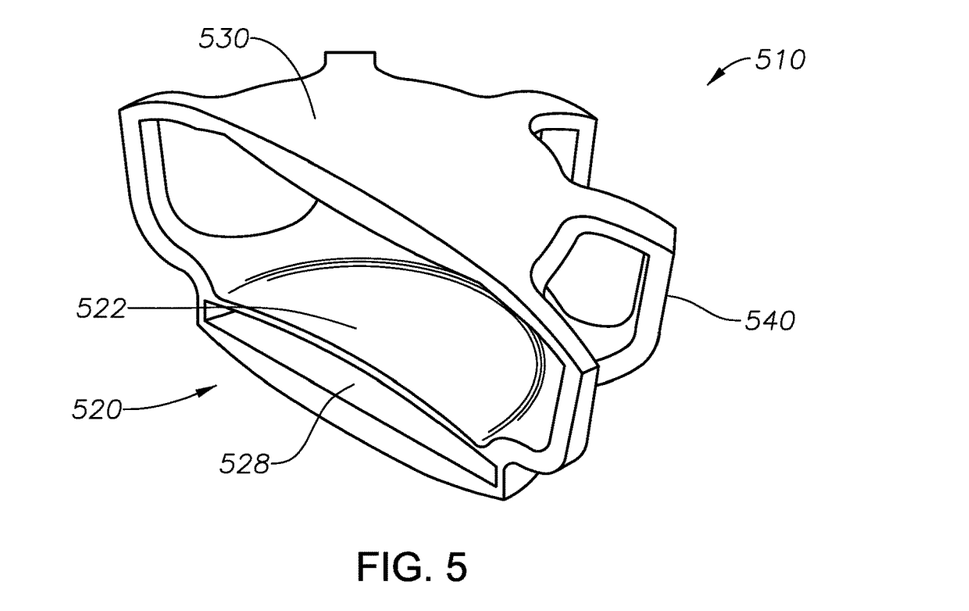
FIG. 5 is a perspective, cross-sectional view of another exemplary curvature-changing, accommodative intraocular lens, according to certain embodiments of the present disclosure.

With reference now to FIG. 5, another exemplary IOL 510 is depicted. The IOL 510 is substantially similar to the IOL 10 depicted in FIG. 1 in that it includes a fluid optic body 520, a second optic body 530, and a plurality of struts 540 extending therebetween. Similarly, the fluid optic body 520 defines a cavity 528 for containing a fluid and is configured to change shape upon axial compression of the IOL 510 due to movement of the struts 540. The IOL 510 differs, however, in that adjacent struts 540 are not coupled to one another at a location between fluid optic bodies 520 and second optic body 530 (e.g., via a ring 46 as shown in FIG. 1). Although the ring 46 can provide stability in some aspects, a lens such as IOL 510 lacking such a ring may ease implantation (e.g., by allowing the IOL 510 to be folded into a more compact shape) and may ease viscoelastic removal. In certain embodiments, the dimensions of IOL 510 may be have a greater overall diameter relative to IOL 10 so as to extend more radially within the capsular bag, thereby increasing stability of the IOL 510 (e.g., by reducing rotation) following implantation.

Figure 6:
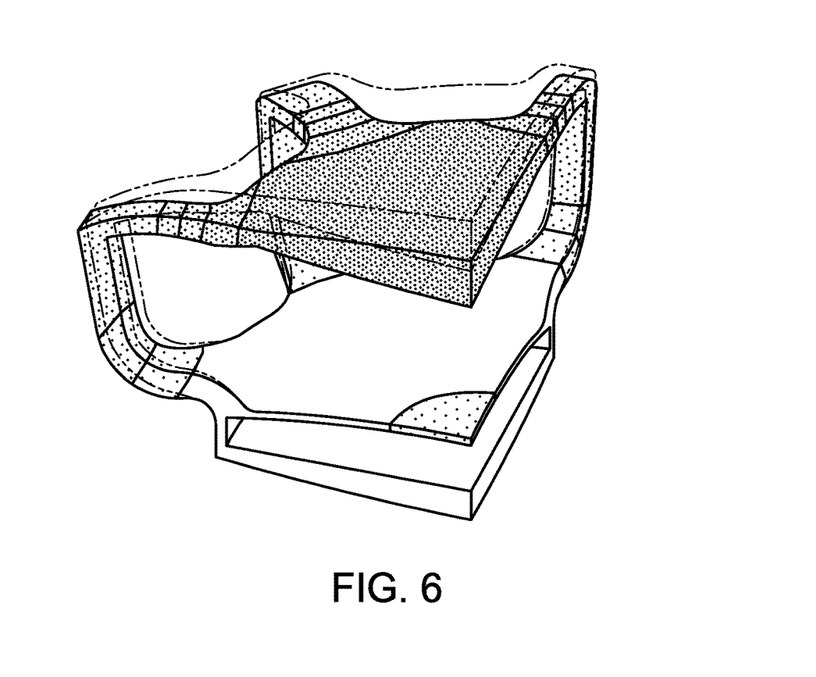
FIG. 6 is a simulation of the movement of the exemplary lens of FIG. 6 as it moves from its resting or accommodated state to its disaccommodated state.

With reference now to FIG. 6, finite element analysis of exemplary simulated movement of the IOL 510 is depicted as the lens 510 moves from its resting or accommodated state (as shown in phantom outline) to its disaccommodated state (as shown in solid color). Upon axial compression of the capsular bag, the axial compressive force on the IOL 510 initiates movement of the second optic body 530 and thus rotation and/or bowing out of struts 540. This rotation results in a radial force applied to the deformable optical membrane 522 such that the cavity 528 containing the optical fluid changes shape, thereby altering the power of the fluid optic body 520.

Figure 7:
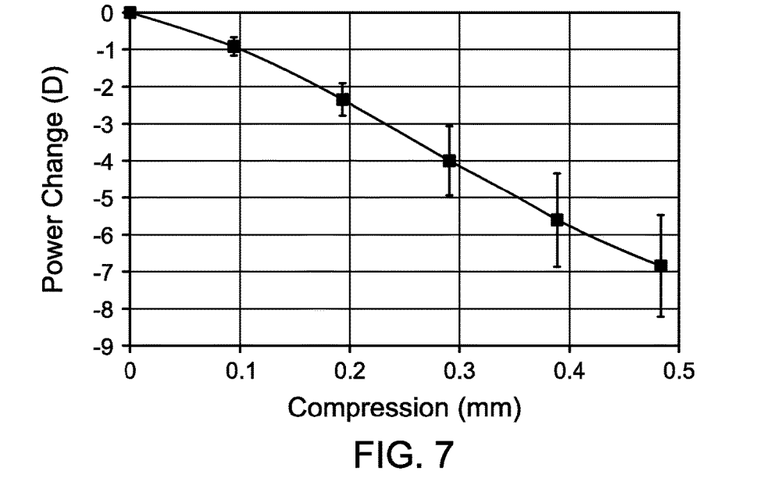
FIG. 7 is a plot depicting the power change of the exemplary lens of FIG. 6 as it moves from its resting or accommodated state to its disaccommodated state.

With reference now to FIG. 7, an exemplary simulation depicts the optical power change of the exemplary IOL 510 as it moves from its accommodated state to its disaccommodated state. As the lens 510 is compressed from its accommodated state (compression=0 mm) to its disaccommodated state (compression=0.5 mm), the IOL 510 exhibits an optical power change of −7 diopter, which is a decrease in the focusing power (for far vision as the light rays from far objects are more parallel relative to those from near objects).

Figure 8:
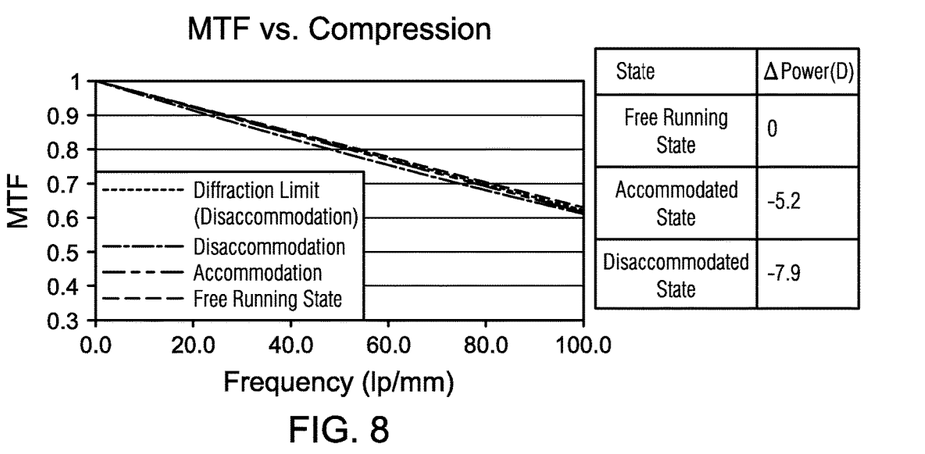
FIG. 8 depicts data showing the modulation transfer function and power change of the exemplary lens as shown in FIG. 1.

With reference now to FIG. 8, a simulated modulation transfer function (MTF) and power change is depicted for a lens in accordance with FIG. 5. The simulation was performed with a 3 mm pupil and a model eye. In the simulation, a simple spherical convex type membrane is used. Since dynamic aberrations are reasonably compensated by the membrane, all MTF curves are close to the diffraction limited MTF over ~8D power change.

Figure 9:
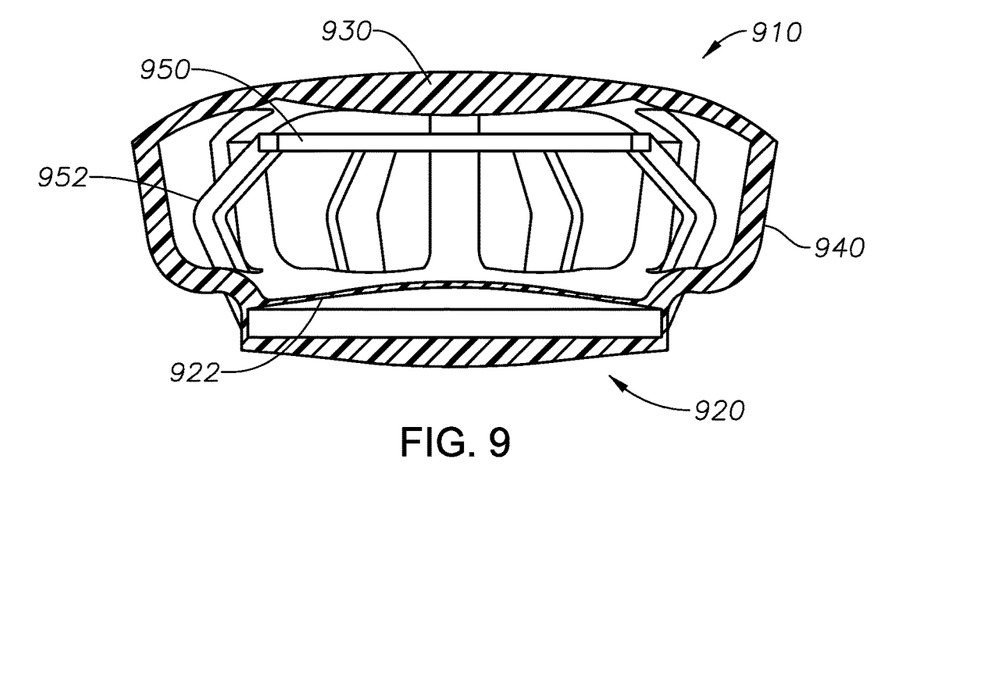
FIG. 9 is a cross-sectional view of another exemplary curvature-changing, accommodative intraocular lens, according to certain embodiments of the present disclosure.

With reference now to FIG. 9, another exemplary IOL 910 is depicted. IOL 910 may be substantially similar to IOL 510 depicted of FIG. 5, but differing in that the IOL 910 additionally includes a mechanical block 950 configured to limit relative axial movement of fluid optic body 920 and second optic body 930. In certain embodiments, mechanical block 950 comprises a ring structure disposed around the optical axis between the second optic body 930 and the fluid optic body 920 such that the ring structure constrains or interferes with axial movement of the second optic body 930 toward the fluid optic 920 after a selected amount of deformation. In certain embodiments, mechanical block 950 may be supported by a second plurality of struts 952 which extend from the fluid optic body 920 at locations between the plurality of struts 940 supporting the second optic body 930. The second plurality of struts 952 may provide increased resistance to compressive force as compared to struts 940 (e.g., by using a stiffer/less-flexible material or by having an increased thickness). Thus, when the second optic body 930 is compressed against the mechanical block 950, further compression of the IOL 910 is resisted, thereby preventing further rotation of the struts 940, and ultimately, further deformation of the deformable membrane 922.

Figure 10:
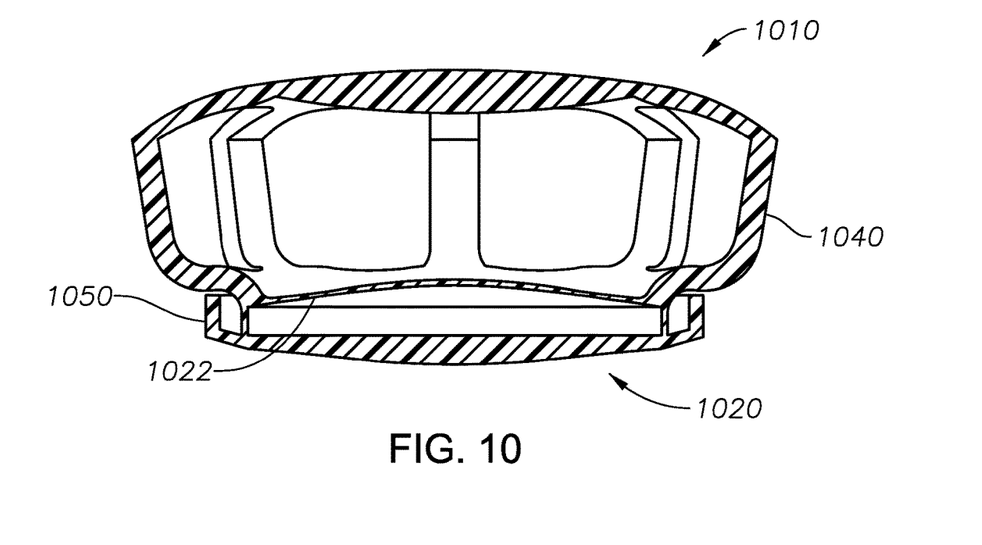
FIG. 10 is a cross-sectional view of another exemplary curvature-changing, accommodative intraocular lens, according to certain embodiments of the present disclosure.

FIG. 10 depicts another exemplary embodiment of an IOL 1010 that includes a mechanical block 1050 differing from that of FIG. 9 in that it physically interferes with the rotation of the struts 1040. For example, as shown in FIG. 10, the fluid optic body 1020 includes a second sidewall 1050 that extends radially beyond the sidewall 1026 such that the posterior portion of the struts 1040 contacts the second sidewall 1050 after a certain level of axial compression. Thus, when the struts 1040 are compressed against the mechanical block 1050, further movement of the struts 1040 is constrained, thereby preventing further deformation of the deformable membrane 1022, as discussed in detail above.

Figure 11:
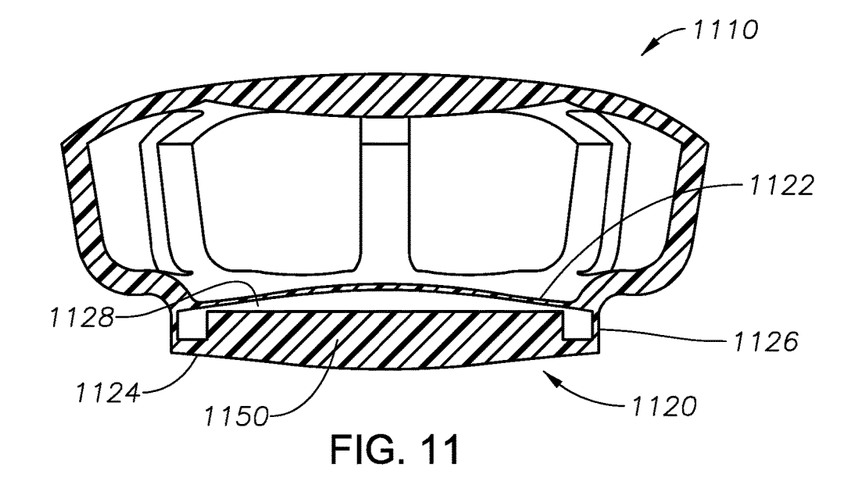
FIG. 11 is a cross-sectional view of another exemplary curvature-changing, accommodative intraocular lens, according to certain embodiments of the present disclosure.

Alternatively or additionally, deformation of the deformable membrane may be controlled by limiting the movement of the deformable membrane directly. For example, with reference not to FIG. 11, another exemplary IOL 1110 having a mechanical block 11150 is depicted. Mechanical block 1150 may interfere with the curvature change that can be exhibited by the deformable optical membrane 1122. The second optical membrane 1124 of IOL 1110 may differ from the second optical membrane 24 of IOL 10 (described with respect to FIG. 1) in that the second optical membrane 1124 may comprise a solid portion extending towards the deformable optical membrane 1122 (i.e., within the cavity 1128). As such, the movement of the deformable optical membrane 1122 can be constrained from moving beyond the surface profile of the mechanical block. Although the mechanical block 1150 is shown as being planar, the present disclosure contemplates that the mechanical block 1150 may have any suitable shape (e.g., mechanical block 1150 may be convex to limit the deformation of the membrane 1122, depending on the desired optical power change).

Figure 12:
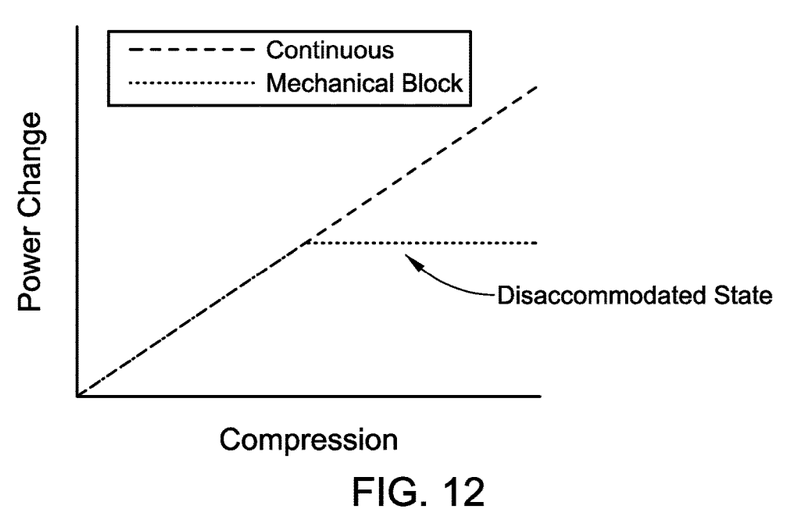
FIG. 12 is a graph depicting power changes as a function of compressive force for exemplary curvature-changing, accommodative intraocular lens with and without mechanical blocks, according to certain embodiments of the present disclosure.

In addition to the structural stability noted above, the mechanical blocks described herein may also provide a consistent, maximum change at various levels of compression and/or prevent refractive errors that typically occur at higher levels of power change. With reference to the graph depicted in FIG. 12, for example, though the IOLs described herein may be subject to additional compressive force, the power change of the IOL may nonetheless remain substantially constant as the mechanical blocks can provide an equivalent resistive force that prevents further compression of the IOLs. Although such action may limit the maximum power change that can be achieved (as shown in the dotted line of FIG. 12), the mechanical blocks can advantageously provide a consistent maximum deformation. Moreover, failure or aberrations (e.g., high refractive errors) that can result, for example, by over-tensioning the deformable optical membranes, can be avoided by limiting the maximum allowable deformation of the deformable optical membrane.

As noted above, the IOLs described herein generally provide a space between the optic bodies and struts within which a solid lens can be disposed. Whereas the curvature of the deformable optical membrane (e.g., deformable optical membrane 22 of FIG. 1) is generally responsible for the optical power of the IOL, a solid lens disposed within the space can additionally provide for power change or other features (e.g., spherical, aspheric, toric features), as is known in the art. To further aid delivery, the solid lens can also be elastomeric or foldable to ease insertion into the capsular bag. Additionally or alternatively, a second optic body of the IOLs described herein can provide for such spherical, aspherical, or toric features, as noted above.

In use, the exemplary accommodative intraocular lenses described herein are adapted to be inserted in the human eye using conventional surgical techniques modified in accordance with the present teachings. Typically, the natural crystalline lens is first removed and the IOL can be folded into a compact size for insertion through an incision or opening in the capsular bag. Following insertion, a single piece IOL (e.g., IOL 10) can be manipulated to assume its proper position in the capsular bag, as described above. Alternatively, an IOL in which multiple components are delivered to the capsular bag independently can be assembled in situ (e.g., by coupling the struts 40 to a fluid optic body 20 delivered independently). In some aspects, the IOLs described herein can be implanted in the capsular bag without optical fluid contained within the cavity of the fluid optic body such that the method for implantation can further include filling the cavity with the optical fluid while the lens is disposed within the eye (e.g., via injection). In this manner, implantation of the exemplary IOLs described herein can aid in restoring natural vision by providing an accommodative, curvature-changing refractive lens that mimics how the natural crystalline lens changes shape in response to movement of the ciliary bodies to variously bend incoming light onto the retina depending on the desired focal point.

The term intraocular lens or "IOL" is used herein to refer to any lens or lens component adapted to be inserted into a patient's eye. Such a lens can be phakic or aphakic (also referred to in the art as pseudophakic) to restore, improve, or partially correct vision. Phakic lenses are used in conjunction with the natural lens of an eye to correct refractive errors such as myopia (near-sightedness), hyperopia (far-sightedness) and astigmatism, coma or other higher order refractive errors (blurred vision due to poor light focusing on the retina due to an irregularly shaped cornea or, in some instances, an irregularly shaped natural lens). An aphakic or pseudophakic lens is inserted in the eye subsequent to removal of the natural lens due to disease, e.g., a cataract or clouding of the natural lens. The aphakic or pseudophakic lens can also restore, improve, or partially correct vision by providing a power comparable to that of the natural lens and can also correct myopia, hyperopia or other refractive errors. Either type of lens may be implanted in the anterior chamber in front of the iris or in the posterior chamber behind the iris and in front of the natural lens or in the region where the natural lens was before removal.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An intraocular lens configured to be implanted within a capsular bag of a patient's eye, the lens comprising:
   a fluid optic body comprising a cavity for containing an optical fluid, the cavity defined by:
      a deformable optical membrane configured to extend across an optical axis of the patient's eye, the deformable optical membrane defining an anterior surface of the cavity;
      a second optical membrane configured to extend across the optical axis of the patient's eye, the second optical membrane defining a posterior surface of the cavity; and
      a sidewall having an anterior end connected to the deformable optical membrane and a posterior end connected to the second optical membrane such that the sidewall extends between the deformable optical membrane and the second optical membrane;
   a second optic body spaced a distance apart from the fluid optic body and configured to extend across the optical axis of the patient's eye; and
   a plurality of struts extending from the sidewall and coupling the fluid optic body to the second optic body, the struts being configured such that axial compression of the capsular bag causes the plurality of struts to rotate the sidewall about a pivot in a manner that increases a diameter of the cavity at the anterior end of the sidewall more than a diameter of the cavity at the posterior end of the sidewall such that a radius of curvature of the deformable optical membrane is increased.

2. The intraocular lens of claim 1, wherein the fluid optic body is configured to be disposed in contact with a first surface of the capsular bag and the second optic body is configured to be disposed in contact with a second surface of the capsular bag.

3. The intraocular lens of claim 1, wherein the rotation of the sidewall in the manner that increases the diameter of the cavity at the anterior end of the sidewall causes an increase in tension on the deformable optical membrane.

4. The intraocular lens of claim 3, wherein the rotation of the sidewall in the manner that increases the diameter of the cavity at the anterior end of the sidewall causes the deformable optical membrane to stretch radially.

5. The intraocular lens of claim 1, wherein the struts are configured such that the axial compression of the capsular bag causes deformation of the struts.

6. The intraocular lens of claim 5, wherein the deformation of the struts comprises each of the struts bowing outward relative to the optical axis of the patient's eye.

7. The intraocular lens of claim 5, wherein the deformation of the struts comprises a radius of curvature of each of the struts decreasing.

8. The intraocular lens of claim 1, wherein, upon the axial compression of the capsular bag, the distance between the fluid optic body and the second optic body along the optical axis decreases.

9. The intraocular lens of claim 1, wherein each of the plurality of struts comprises a curved portion that is concave relative to the optical axis.

10. The intraocular lens of claim 1, wherein the second optic body comprises a solid optic.

11. The intraocular of claim 1, wherein the second optic body comprises a second fluid optic body, the second fluid optic body comprising a second cavity for containing a second optical fluid, the second cavity at least partially defined by:
- a second sidewall extending around the second cavity and defining a diameter of the second cavity; and
- a second deformable optical membrane intersecting the second sidewall around a circumference of the second sidewall and spanning the diameter of the second cavity, the second deformable optical membrane configured to extend across the optical axis of the patient's eye;

wherein:
- the plurality of struts extending from the sidewall of the fluid optic body and connect to the second sidewall of the second fluid optic body; and
- the struts are configured such that axial compression of the capsular bag causes the plurality of struts to deform the second sidewall of the second fluid optic body in a manner that increases in the diameter of the second cavity of the second fluid optic body such that a curvature of the second deformable optical membrane of the second fluid optic body is modified.

12. The intraocular lens of claim 1, wherein each of the plurality of struts are coupled to one another via a circumferential ring disposed between the fluid optic body and the second optic body.

13. The intraocular lens of claim 12, wherein the circumferential ring increases in diameter upon the axial compression of the capsular bag.

14. The intraocular lens of claim 1, further comprising a mechanical block defining a minimum distance between the fluid optic body and the second optic body such that the increase in the radius of curvature of the deformable optical membrane is limited.

15. The intraocular lens of claim 14, wherein the mechanical block comprises a second plurality of struts extending along the optical axis from the fluid optic body and partially towards the second optic body.

16. The intraocular lens of claim 15, wherein the mechanical block comprises a radial extension from the fluid optic body that limits deformation of the struts during the axial compression of the capsular bag.

17. The intraocular lens of claim 1, further comprising a solid lens disposed between the fluid optic body and the second optic body.

* * * * *